United States Patent [19]

Marsham et al.

[11] Patent Number: 4,568,691
[45] Date of Patent: Feb. 4, 1986

[54] ANTI-INFLAMMATORY ESTERS OF 4-(1-HYDROXY-2-[(ACYLAMINO)-ALKYLAMINO]-ETHYL)-PHENOL DERIVATIVES, COMPOSITIONS, AND METHOD OF USE THEREFOR

[75] Inventors: Peter R. Marsham, Poynton; David S. Thomson, Holmes Chapel, both of United Kingdom

[73] Assignee: Imperial Chemical Industries, PLC, London, England

[21] Appl. No.: 684,253

[22] Filed: Dec. 20, 1984

Related U.S. Application Data

[62] Division of Ser. No. 452,804, Dec. 23, 1982, Pat. No. 4,520,027.

[30] Foreign Application Priority Data

Dec. 23, 1981 [GB] United Kingdom ............ 8138830

[51] Int. Cl.$^4$ ............ A61K 31/34; A61K 31/38; C07D 307/46; C07D 307/80
[52] U.S. Cl. ............ 514/443; 514/448; 514/438; 514/469; 514/471; 549/57; 549/64; 549/65; 549/467; 549/487
[58] Field of Search ............ 549/57, 64, 65, 66, 549/467, 468, 471, 487, 488; 514/443, 448, 469, 471

[56] References Cited

U.S. PATENT DOCUMENTS 3,686,206 8/1972 Posselt et al. .................. 549/488
4,303,649 12/1981 Jones .................. 424/177
4,323,575 4/1982 Jones .................. 424/267
4,355,045 10/1982 Preston et al. .................. 424/322

FOREIGN PATENT DOCUMENTS 1591618 1/1971 United Kingdom ............ 560/138

OTHER PUBLICATIONS

Jones et al., CA, vol. 89, 1978, 89:129233V, p. 564.

Primary Examiner—Henry R. Jiles
Assistant Examiner—J. G. Mullins
Attorney, Agent, or Firm—Cushman, Darby & Cushman

[57] ABSTRACT

The invention concerns novel esters of 4-(1-hydroxy-2-[(acylamino)alkylamino]ethyl)phenols of the formula:

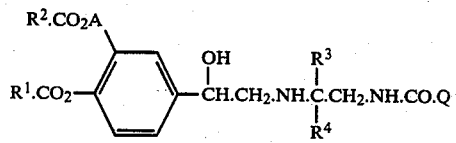

and salts thereof, wherein $R^1$ and $R^2$ are (3–5C)alkyl, $R^3$ and $R^4$ are hydrogen or methyl, A is a direct bond or methylene, and Q is various heteroaromatic containing groups. The esters possess topical anti-inflammatory properties and the invention provides pharmaceutical compositions containing the esters and processes for their chemical manufacture.

10 Claims, 12 Drawing Figures

EXAMPLE I
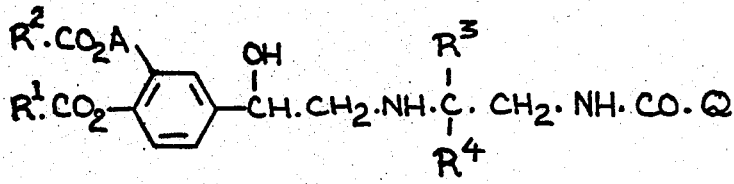
EXAMPLE II
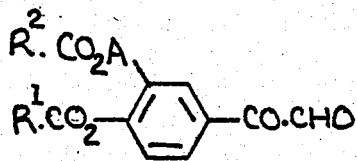
EXAMPLE III
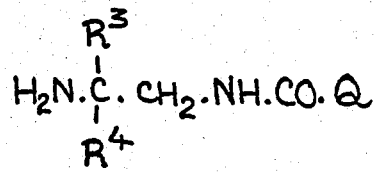
EXAMPLE IV
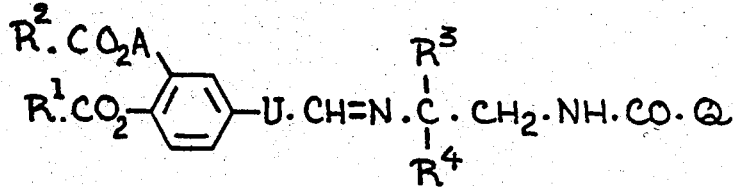
EXAMPLE V
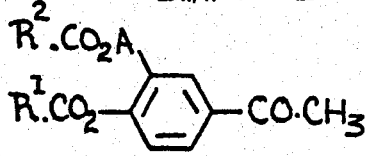
EXAMPLE VI
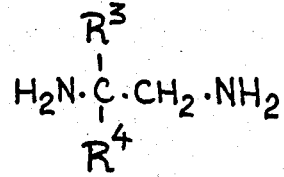
$Q \cdot CO_2H$
EXAMPLE VII

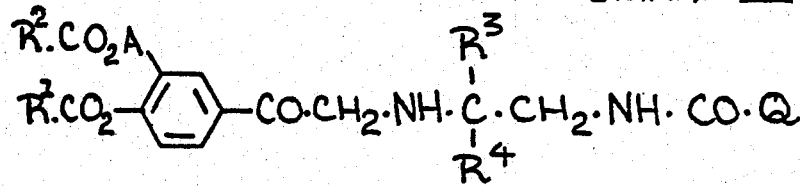
EXAMPLE VIII
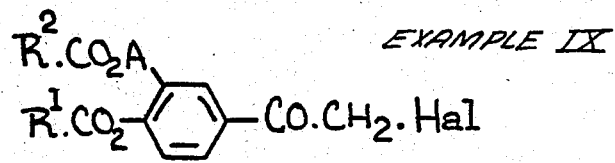
EXAMPLE IX
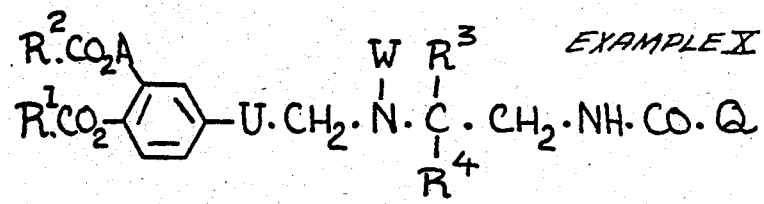
EXAMPLE X
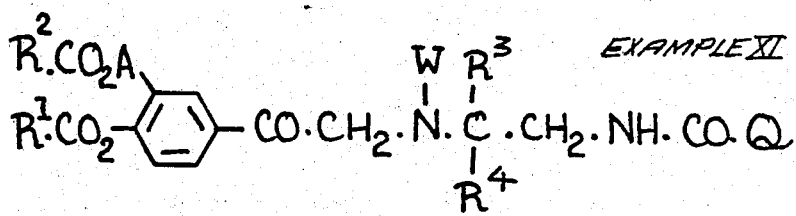
EXAMPLE XI
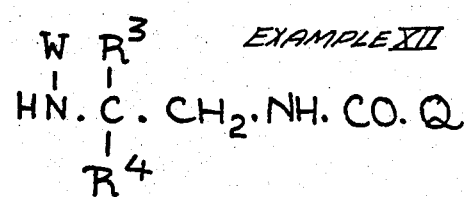
EXAMPLE XII

ANTI-INFLAMMATORY ESTERS OF 4-(1-HYDROXY-2-[(ACYLAMINO)-ALKYLAMINO]-ETHYL)-PHENOL DERIVATIVES, COMPOSITIONS, AND METHOD OF USE THEREFOR

This is a division of application Ser. No. 452,804, filed Dec. 23, 1982 now U.S. Pat. No. 4,520,027.

This invention concerns novel phenol esters and, more particularly, novel esters of various 4-(1-hydroxy-2-[(acylamino)alkylamino]ethyl)phenols, which esters possess anti-inflammatory properties when applied topically to an area of inflammation i.e. topical anti-inflammatory properties.

It is known from our earlier patent publications that esters of certain 4-(1-hydroxy-2-[(acylamino)alkylamino]ethyl)phenols, in which the acyl contains an aromatic group, possess topical anti-inflammatory properties (UK patent specification Ser. No. 1591618). Such esters are typified by the known compound 4-(1-hydroxy-2-[2-methyl-2-(phenoxyacetamido)-propylamino]ethyl)catechol dipivaloyl ester, which possesses potent topical anti-inflammatory properties. Unfortunately, this compound like many of the known, potent topical anti-inflammatory diesters of catechol derivatives, exhibits a significant reduction in topical anti-inflammatory properties after two or more topical applications of diester spaced over several days, as indicated in the standard laboratory test mentioned hereinafter. Consequently, it is expected that such diesters will only find therapeutic application at relatively low application rates in the treatment of generally minor, non-chronic, inflammatory skin diseases and skin conditions.

We have now discovered (and herein lies the basis for our invention) a relatively small number of novel 4-(1-hydroxy-2-[(acylamino)alkylamino]ethyl)phenol esters, structurally similar to the prior art diesters, but in which the acyl contains a limited range of heteroaromatic groups, and which novel esters show no significant reduction in topical anti-inflammatory properties after several topical applications at relatively high concentration, spaced over several days in the standard laboratory test mentioned hereinafter.

According to the invention there is provided a diester of the formula I wherein $R^1$ and $R^2$ are independently (3–5C)alkyl; and (i) A is a direct bond, $R^3$ and $R^4$ are hydrogen, and Q is 2-thienyl, 2-benzo[b]thienyl, 2-thienylmethyl, 3-pyridyl, 4-pyridyl or 2-pyridylmethyl;
(ii) A is a direct bond, $R^3$ and $R^4$ are methyl, and Q is 2-furyl, 3-pyridyl, 2-pyridylmethyl, 2-benzo[b]furyl or 2-benzo[b]thienyl; or
(iii) A is methylene, $R^3$ and $R^4$ are methyl and Q is 2-benzo[b]furyl or 2-benzo[b]thienyl;

or a pharmaceutically acceptable acid-addition salt thereof.

It will be observed that the compounds of formula I possess at least one asymmetric carbon atom, that is the benzylic carbon atom bearing the hydroxy substituent. The compounds of formula I can therefore exist in racemic and optically active forms. This invention relates to the racemic form of a compound of formula I and to any optically-active form which possesses useful topical anti-inflammatory properties, it being well known how to obtain optically-active forms by resolution of a racemic form or by synthesis from optically-active starting materials, and how to determine the topical anti-inflammatory properties by the standard tests described hereinafter.

A particular value for $R^1$ or $R^2$ is, for example, isopropyl, n-propyl, isobutyl, t-butyl, n-butyl or 2,2-dimethylpropyl, of which values t-butyl is generally preferred. $R^1$ and $R^2$ may conveniently have the same value.

Particular groups of esters comprised by the invention are, for example, those compounds of formula I wherein $R^1$ and $R^2$ have any of the meanings stated hereinbefore and in addition (i) A is a direct bond, $R^3$ and $R^4$ are hydrogen, and Q is 2-thienyl, 2-thienylmethyl or 2-benzo[b]thienyl;
(ii) A is a direct bond, $R^3$ and $R^4$ are methyl, Q is 2-furyl, 2-benzo[b]furyl or 2-benzo[b]thienyl;
(iii) A is a direct bond, $R^3$ and $R^4$ are both hydrogen, and Q is 3-pyridyl, 4-pyridyl or 2-pyridylmethyl;
(iv) A is a direct bond, $R^3$ and $R^4$ are both methyl, and Q is 3-pyridyl or 2-pyridylmethyl; or
(v) A is methylene, $R^3$ and $R^4$ are methyl, and Q is 2-benzo[b]furyl or 2-benzo[b]thienyl; together with, in each group, the pharmaceutically acceptable acid-addition salts thereof.

A preferred group of esters comprises those compounds of formula I wherein $R^1$ and $R^2$ have any of the meanings stated above, A is a direct bond, $R^3$ and $R^4$ are both methyl and Q is 2-furyl, 2-benzo[b]-furyl or 2-benzo[b]thienyl; together with the pharmaceutically acceptable acid-addition salts thereof.

A particular pharmaceutically acceptable acid-addition salt of an ester of formula I is, for example, an addition salt with an inorganic acid such as hydrochloric, hydrobromic, phosphoric or sulphuric acid, or with an organic acid such as oxalic, adipic, tartaric, fumaric, citric, acetic, salicyclic, benzoic, naphthoic or methane-sulphonic acid.

Representative esters of the invention are described in the accompanying Examples, but of these the following are of particular interest: 4-(1-hydroxy-2-[1,1-dimethyl-2-(2-furylcarboxamido)ethylamino]ethyl)-catechol dipivaloyl ester, 4-(1-hydroxy-2-[1,1-dimethyl-2-(2-benzo[b]furyl-carboxamido)ethylamino]ethyl)catechol dipivaloyl ester, 4-(1-hydroxy-2-[1,1-dimethyl-2-(2-benzo[b]thienylcarboxamido)ethylamino]ethyl)catechol dipivaloyl ester; preferably as a pharmaceutically acceptable acid-addition salt.

The following chemical procedures are illustrative of the processes which may be used for the manufacture of novel compounds of the formula I and are provided as a feature of the invention $R^1$, $R^2$, $R^3$, $R^4$, and Q have the meanings defined above.

(a) A glyoxal of the formula II or a hydrate thereof is reacted with an amine of the formula III under reducing conditions.

Particular suitable reducing conditions are provided by using, for example, an alkali metal borohydride or cyanoborohydride, for example sodium borohydride or cyanoborohydride, conveniently in an inert solvent or diluent, for example acetonitrile, methanol, ethanol or 2-propanol and at a temperature in the range, for example $-20°$ C. to $30°$ C. When sodium cyanoborohydride is used, the reaction is preferably carried out at or near pH 4, for example in the presence of acetic acid. Other standard reducing conditions may be suitable provided they are compatible with the other substituents present in the starting materials.

It will be appreciated that processes of the above general type are known as reductive alkylations, and proceed at least in part through an intermediate of the formula IV wherein U is hydroxymethylene and/or of the formula IV wherein U is carbonyl. Such an intermediate of formula IV wherein U is a hydroxymethylene or carbonyl (or a mixture of such intermediates) may be prepared and then reduced in two separate stages in process (a) if desired.

The glyoxals of formula II may be obtained, for example, by selenium dioxide oxidation of an acetophenone of the formula V in an appropriate solvent, for example aqueous dioxan, at a temperature in the range, for example, 50°–150° C., optionally followed by hydrate formation.

Alternatively, the glyoxals of formula II may be conveniently obtained by dimethylsulphoxide oxidation of the appropriate phenacyl bromide derived by bromination of the corresponding acetophenone of formula V.

The amines of formula III may be obtained, for example, by reacting a diamine of the formula VI with an acylating agent derived from an acid of the formula VII, for example a chloride or bromide derivative of such an acid. Alternatively, an ethyl or methyl ester of such an acid may be used as acylating agent. In which case, the acylation is generally carried out under the influence of heat, for example at 40°–100° C.

The diamines of formula VI and the acids of formula VII can be obtained by general procedures of organic chemistry.

(b) A ketone of the formula VIII is reduced

The reduction is preferably performed using an alkali metal borohydride such as sodium or potassium borohydride or cyanoborohydride conveniently in an inert solvent or diluent, for example acetonitrile, methanol, ethanol or 2-propanol and at a temperature of, for example, −20° to 30° C. However, other standard reducing conditions known in the art may also be employed provided they are compatible with the other substituents present in the starting material.

The starting ketone of formula VIII may be obtained, for example, by reacting a phenacyl halide of the formula IX wherein Hal. is halogeno (such as chloro or bromo) with an amine of the formula III, conveniently in an inert diluent or solvent, for example ethanol, dioxan, chloroform or acetonitrile, and at a temperature of, for example, 15° to 30° C. An acid-binding agent, such as pyridine, triethylamine or an alkali metal carbonate or hydrogen carbonate, or an excess of the amine of formula III, may conveniently be present.

The phenacyl halides of formula IX may be obtained by standard procedures of organic chemistry.

(c) A benzyl derivative of the formula X wherein U is carbonyl or hydroxymethylene and W is benzyl or substituted benzyl, is hydrogenolysed.

A particular value for W when it is substituted benzyl is, for example, 4-methylbenzyl.

The hydrogenolysis must necessarily be carried out under conditions which do not affect other substituents, and is therefore preferably carried out by means of catalytic hydrogenation, for example with hydrogen in the presence of a palladium, platinum or nickel catalyst in a suitable diluent or solvent, for example 2-propanol, ethanol or water, or a mixture thereof, conveniently at a temperature in the range, for example, 15°–30° C. and optionally under a pressure of up to 5 bars.

It will be appreciated that when U is carbonyl in the starting material of formula X it is usually necessary to carry out the hydrogenolysis under greater than atmospheric pressure of hydrogen so that concomitant reduction of the carbonyl also takes place.

Those starting materials of formula X wherein U is hydroxymethylene may be obtained, for example, by sodium borohydride reduction of the corresponding ketone of the formula XI wherein W has the meaning defined above, using similar solvents and temperatures to those described earlier for process (b). Such starting materials may conveniently be prepared and used in situ in process (c).

The ketones of formula XI (which are also starting materials of formula X wherein U is carbonyl) may themselves be prepared by reaction of the appropriate phenacyl halide of formula IX with an amino compound of the formula XII wherein W has the meanings defined above, using analogous reaction conditions to those described in connection with process (b) for the production of the starting materials of formula VIII.

The amino compounds of formula XII may be conveniently obtained by reductive alkylation of the appropriate amino compound of formula III using the appropriate benzaldehyde and a reducing agent such as sodium cyanoborohydride, and employing similar conditions to those specified hereinbefore for process (a).

A compound of formula I in free base form may be converted into a pharmaceutically acceptable-acid-addition salt by reaction with a suitable acid, as defined hereinbefore, using conventional means which avoid hydrolysis of ester groups. Alternatively, when a hydrogen chloride or bromide salt is required, this may be conveniently obtained by producing a stoichiometric amount of the hydrogen halide in situ by catalytic hydrogenation of the appropriate benzyl halide preferably in an inert solvent or diluent, for example, ethanol and at, or near, room temperature.

The compounds of formula I are conveniently isolated as their acid-addition salts.

Optically-active forms of a compound of formula I may be obtained by conventional resolution of the corresponding racemic form of a compound of formula I. Thus, a racemic form of a compound of formula I may be reacted with an otpically-active acid, followed by fractional crystallisation of the diastereoisomeric mixture of salts thus obtained from a suitable solvent, for example ethanol, whereafter the optically-active form of a compound of formula I may be liberated by treatment under conditions which avoid loss of any sensitive ester groups, for example by using anion exchange chromatography. A particularly suitable optically-active acid is, for example (+)- or (−)-tartaric acid, (+)- or (−)-0, 0-di-p-toluoyl-tartaric acid, or (−)-2,3,,4,5di-0-isopropylidene 2-keto-L-gulonic acid.

As stated above, the esters of formula I possess anti-inflammatory properties when applied topically to an area of inflammation. These anti-inflammatory properties may be demonstrated, for example, in a standard test involving the inhibition of croton oil induced inflammation on the mouse ear. The activity of an individual ester in this test depends upon its particular chemical structure, but in general esters of formula I produce a significant inhibition of the inflammation at a topically applied dose of 0.30 mg. per ear or much less.

The effect of repeated application of a test compound on its anti-inflammatory properties in this test may routinely be assessed by applying the test compound daily at a concentration four times greater than the $IC_{50}$ (concentration necessary to produce a 50% reduction in the croton oil induced inflammation) for that compound, over at least 2–4 days. Comparison of the percentage reduction in inflammation on, for example, day 1 and 4 gives a measure of any fall in anti-inflammatory properties on repeated topical application of a test-compound.

The esters of formula I mentioned herein generally show no significant reduction in anti-inflammatory effect in the mouse croton oil inflammation test after two or more topical applications spaced apart by several days.

Another standard test in which the anti-inflammatory properties of an ester of formula I may be demonstrated involves the inhibition of oxazolone induced contact sensitivity, for example, on the mouse ear or pig back. In general, esters of formula I produce significat inhibition of the inflammation in the mouse ear oxazolone test at a topically applied dose of 0.25 mg. per ear, or much less.

No overt toxic effects were detected at the active doses in either of the above tests, with the esters of formula I described herein.

It is envisaged that the esters of the invention will be of value in the treatment of both acute and chronic inflammatory diseases or inflammatory conditions affecting the skin of warm-blooded animals (including man), for example in psoriasis, eczema, urticaria, contact dermatitis, atopic dermatitis, inflammatory dermatoses, sun-burn and insect bites, as a result of their particular combination of topical anti-inflammatory properties. In general, the esters of the invention may be used in the treatment of inflammatory diseases or inflammatory conditions affecting the skin in an analogous manner to that in which known topically active anti-inflammatory agents, for example the topically active steroids, are used.

When used for the topical treatment of an area of inflammation affecting the skin of a warm-blooded animal, for example man, an ester of formula I may be administered topically at a dose in the range 10 μg. to 10 mg./cm², or at an equivalent dose of a pharmaceutically acceptable acid-addition salt thereof, and, if necessary, a dose in this range is repeated at intervals of, for example, 4–12 hours. However, it will be appreciated that the total daily amount of ester of formula I administered necessarily depends on the extent and severity of the inflammatory disease or condition under treatment.

The esters of formula I may be administered in the form of pharmaceutical compositions and according to a further feature of the invention there is provided a pharmaceutical composition comprising an ester of formula I, or a pharmaceutically acceptable acid-addition salt thereof, in association with a pharmaceutically acceptable excipient in a form suitable for topical administration, for example in the form of an ointment, gel, aqueous or oily solution or suspension, emulsion or aerosol formulation. Such pharmaceutical compositions may contain for example 0.05% to 5% w/w of an ester of formula I, or an equivalent amount of a pharmaceutically acceptable acid-addition salt thereof, hereinafter referred to as an active ingredient.

The pharmaceutical compositions may be made by methods well known in the art for the production of topical formulations, using conventional pharmaceutically acceptable excipients.

Thus, a particular ointment formulation may be prepared by dispersing an active ingredient as defined above in a suitable organic diluent, for example soft paraffin, optionally in the presence of an emulsifying and/or thickening agent, for example sorbitan monostearate.

A particular gel formulation may be prepared by adding a gelling agent, for example carboxy-polymethylene, to a solution of an active ingredient as defined above in a suitable organic solvent, for example 2-propanol.

A particular emulsion formulation, for example a cream or a lotion, may be prepared by mixing an active ingredient as defined above with a suitable conventional emulsifying system and water.

The pharmaceutical composition may also conveniently contain one or more other conventional excipients, for example a solubilising agent such as polyethylene glycol, propylene glycol, diethylene glycol monomethyl or monoethyl ether, or benzyl alcohol, and/or a penetration enhancer such as dimethyl sulphoxide, N-methylpyrrolidin-2-one, or 1-dodecyl-hexahydro-2H-azepin-2-one, and/or conventional stabilising agents and antioxidants, in order to produce a stable topical formulation which results in significant absorption of the active ingredient into the skin. Other conventional excipients, such as colouring agents, dispersing agents or preservatives, may also be present.

In addition a pharmaceutical composition according to the invention may desirably contain, as well as an active ingredient defined above, at least one known pharmaceutical agent, such as a corticosteroid, phosphodiesterase inhibitor, anti-bacterial agent, anti-fungal agent, anti-histamine, local anaesthetic or an emollient.

The invention is illustrated but not limited by the following Examples in which:

(i) Unless otherwise stated, all procedures were carried out at room temperature (in the range 18 20 –26° C.) and at atmospheric pressure; and all evaporations were performed by rotary evaporation under reduced pressure;

(ii) Nuclear magnetic resonance (NMR) data, where given, is presented in the form of chemical shifts (delta values) for characteristic protons, relative to tetramethylsilane as standard determined in $d_6$DMSO as solvent and at 100 MHz;

(iii) Column chromatography was performed on silica gel (Kieselgel 60; ART 9385) obtainable from E. Merck of Darmstadt, West Germany;

(iv) Yields, where given, are purely illustrative and are not to be construed as the maximum attainable; and (v) All crystalline end-products had satisfactory microanalyses.

EXAMPLE 1

Powdered 2-bromo-3',4'-di-(pivaloyloxy)-aceto-phenone (3.0 g.) was added in one portion to a stirred solution of N-(2-aminoethyl)thiophene-2-carboxamide (2.56 g.) in dry dioxan (20 ml.). The resulting mixture was stirred for 15 minutes and then filtered through diatomaceous earth to remove any oily precipitate. The filtrate [containing 4-(2-[2-thienylcarboxamido)ethyl amino]acetyl)catechol dipivaloyl ester] was immediately added to ice cold ethanol (30 ml.) containing sodium borohydride (0.57 g.). The residue from the filtration was washed with ether (15 ml.) and the washings were added to the ethanol/borohydride reaction mixture. This mixture was stirred for 30 minutes at 0° C., then diluted with saturated brine (50 ml.) and extracted with ether (2×100 ml.). The extracts were washed with brine, dried (MgSO$_4$) and evaporated to give a brown oil which was chromatographed on a column of Kieselgel 60 (30 g.), eluting initially with chloroform and then with 10% v/v methanol in chloroform. There was thus obtained 4-(1-hydroxy-2-[2-(2-thienylcarboxamido)ethylamino]ethyl)catechol dipivaloyl ester (A) (0.60 g.) as its oily free base. This was dissolved in the minimum volume of ether containing a few drops of ethanol. The solution obtained was treated with a slight excess of ethereal hydrogen bromide, and the mixture was evaporated. The residue was washed with ether and then dried under high vacuum to give the hydrobromide salt of (A) (0.53 g.) as a foam; NMR: 7.64–7.81 (2H, complex, thiophene H); 7.02–7.26 (4H, complex, Ph + thiophene H); 5.0 (1H, complex, CH.OH); 2.91–3.70 (6H, complex, 3×CH$_2$NH); 1.20 [18H, singlet, (CH$_3$)C]; microanalysis, found: C, 51.4; H,6.0; N,4.6% C$_{23}$H$_{34}$N$_2$O$_6$S. HBr.0.5H$_2$O requires C,51.7; H,6.2; N, 4.8%.

The starting carboxamide was prepared as follows:

A mixture of ethyl thiophene-2-carboxylate (12.0 g.) and ethylenediamine (15.4 ml.) was heated at 95–100° C. for 48 hours. Excess ethylenediamine was removed under reduced pressure and the residue was dissolved in water (150 ml.). The insoluble material [bis(carboxamide)derivative] was removed by filtration. Evaporation of the filtrate gave a residue which was dissolved in toluene (50 ml.). The mixture was evaporated to give N-(2-aminoethyl)-thiophene-2-carboxamide as an oil (12.0 g.) essentially pure by TLC (R$_f$ 0.90; SiO$_2$: 10% v/v methanol in chloroform as eluant) which was used without purification.

EXAMPLES 2-4

Using a similar procedure to that described in Example 1 but starting from the appropriate amine of formula III and with intermediate formation of the corresponding ketone of formula VIII as its hydrobromide salt, the following compounds of formula I (R$^1$=R$^2$=t-butyl; R$^3$=R$^4$=H; A=direct bond) may be obtained in yields of 20–25%:

| Example | Q | m.p. (°C.) | Isolated form | NMR* |
|---|---|---|---|---|
| 2 | 2-thienylmethyl | HBr salt + 2.5 H$_2$O | foam | 7.1–7.3 (2H, complex); 6.80 (1H,d); 3.60 (2H,s, CH$_2$ thiophene) |
| 3 | 2-benzo[b]thienyl | free base + 0.5 CHCl$_3$ | 70–77 | 7.2–8.3 (5H complex) |
| 4 | 4-pyridyl | HBr salt | 118–122 | 8.80 (2H,dd); 7.99 (2H,dd) |

Note*: The following NMR signals were common to each compound:
7.0–7.4 (3H, complex, aromatic H); 4.7–5.0 (1H, complex, CHOH); 2.6–3.8 (6H, complex, 3 × CH$_2$NH); 1.20 [18H, s, (CH$_3$)$_3$.C.]

The necessary starting amines of formula III were obtained using a similar procedure to that described for the analogous amine in Example 1 but starting from the appropriate ester of the formula Q.CO$_2$R wherein R is methyl or ethyl. The amines of formula III were thus obtained as their oily free bases which were essentially pure on thin layer chromatography (TLC) (SiO$_2$: 10–20% v/v methanol in chloroform) and were used without further purification.

EXAMPLE 5

A solution of 4-(1-hydroxy-2-[N-benzyl-2-(3-pyridylcarboxyamido)ethylamino]ethyl)cathechol dipivaloyl ester (2.28 g.) in ethanol (30 ml.) was stirred for 90 minutes at 80° C. in an atmosphere of hydrogen in the presence of 10% w/w palladium on carbon (0.75 g.). The solution was cooled, filtered and the filtrate was evaporated. The brown gum obtained was purified by chromatography on a column of Kieselgel 60 (50 g.), using chloroform containing 2-10% v/v methanol as eluant to yield 4-(1-hydroxy-2-[2-(3-pyridylcarboxamido)ethylamino]ethyl)catechol dipivaloyl ester (B) (1.18 g.) as a gum. This was dissolved in the minimum volume of ether containing a few drops of ethanol. The solution obtained was treated with a slight excess of ethereal hydrogen bromide and evaporated. The residue was triturated with ether to give (B) as its dihydrobromide salt (1.15 g.), m.p. 135;14 136° C. (hemihydrate), having NMR: 9.40 (1H,s,pyridine-2H(; 90(1H,d,pyridine-6H); 8.90 (1H,d,pyridine-4H); 8.05 (1H,dd,pyridine-5H); 7.12–7.45 (3H,complex, phenyl-H); 5.05 (1H,d, CHOH); 3.00–3.85 (6H, complex, 3×CH$_2$NH); 1.25 [18H,s,(CH$_3$)$_3$C]; microanalysis, found: C,47.3; H,5.5; N,6.4% C$_{26}$H$_{35}$N$_3$O$_6$.2HBr.0.5H$_2$O requires: C,47.5; H,5.8; N,6.4%.

The starting material was prepared as follows:

A mixture of ethyl nicotinate (21.9 g.) and ethylenediamine (30 ml.) was heated to 100° C. for 16 hours under an atmosphere of argon. Excess ethylenediamine was removed by distillation in vacuo and the residue was dissolved in water (100 ml.) The insoluble material [bis(-carboxamido)derivative] was removed by filtration. Evaporation of the filtrate, addition of toluene (50 ml.) followed by re-evaporation gave crude N-(2-aminoethyl)pyridine-3-carboxamide (26.5 g.) as its oily free base, essentially pure by TLC (SiO$_2$: 10% MeOH/CHCl$_3$) and which was used without purification.

A solution of N-(2-aminoethyl)pyridine-3-carboxamide (26.5 g.) and benzaldehyde (16.35 ml.) in ethanol (220 ml.) was kept for 48 hours. A small quantity of solid was removed by filtration. Sodium borohydride (6.1 g.) was then added to the filtrate which was stirred for 1 hour. Glacial acetic acid was then added cautiously until the solution was neutral. The solution was diluted with water (100 ml.) and basified with 2M sodium hydroxide. The mixture was extracted with ethyl acetate (3×200 ml.) and the extracts washed with saturated brine, dried (Na$_2$SO$_4$) and evaporated. The residue was purified by chromatography on a column of Florisil (200 g.), eluting with ethyl acetate, to yield N-[2-(benzylamino)ethyl]pyridine-3-carboxamide (29.5 g.) as a pale brown oil.

A solution of 2-bromo-3',4'-di(pivaloyloxy)-acetophenone (3.99 g.) and N-[2-benzylamino)ethyl]-pyridine-3-carboxamide (5.10 g.) in dry dioxan (30 ml.) was stirred for 5 hours. The reaction mixture was diluted with ether (150 ml.) and the finely divided precipitate was separated by filtration. The filtrate was washed with water, then brine, dried (Na$_2$SO$_4$) and evaporated to give 4-(2-[2-(N-benzyl-2-[3-pyridyl-carboxamido])ethylamino]acetyl)catechol dipivaloyl ester (C) as a brown oil which was used without purification.

A solution of (C) (5.7 g.) in 2-propanol (50 ml.) was stirred at −10° C. during the addition of sodium borohydride (0.57 g.). Methanol (15 ml.) was then added followed by a further portion of sodium borohydride (0.57 g.). The reaction mixture was then stirred for 30 minutes at −10° C. and diluted with water (100 ml.). The aqueous layer was extracted with ether (2×100 ml.). The combined ether layer and extracts were washed with water, then brine, dried ($Na_2SO_4$) and evaporated. The resulting oil was purified by chromatography on a column of Kieselgel 60 (40 g.), eluting with 49:1 v/v chloroform/methanol, to yield 4-(1-hydroxy-2-[N-benzyl-2-(3-pyridylcarboxamido)-ethylamino]ethyl)catechol dipivaloyl ester (2.28 g.) as a golden yellow gum, essentially pure by TLC ($SiO_2$; 10% v/v methanol in chloroform) which was used without full characterisation.

EXAMPLE 6

The process described in Example 5 was repeated starting with the analogous N-benzyl derivative of formula X (U=hydroxymethylene, Q=2-pyridylmethyl). There was thus obtained 4-(1-hydroxy-2-[2-(2-pyridylacetamido)ethylamino]ethyl)catechol dipivaloyl ester, as its hydrobromide salt isolated as a foam in 22% yield: NMR: 8.80 (1H,d), 8.30 (1H,t), 7.80 (1H,d), 7.0–7.4 (4H, complex, aromatic H+pyridine H), 4.7–5.0 (1H, complex, C$\underline{H}$OH), 3.5 (2H,s, C$\underline{H}_2$ pyridine), 2.6–4.0 (6H, complex, $3\times C\underline{H}_2NH$), 1.2[18H,s,$(CH_3)_3C$].

The necessary starting material of formula X was obtained in a similar manner to that described in Example 5 but starting from the ethyl ester of 2-pyridylacetic acid. The starting material of of formula X was thus obtained as its oily free base which was essentially pure by TLC ($SiO_2$: 10% v/v methanol in chloroform) and was used without purification.

EXAMPLE 7

A solution of 3′,4′-di-(pivaloyloxy)phenyl-glyoxal (3.67 g.), N-(2-amino-2-methylpropyl)furan-2-carboxamide (2.0 g.) and glacial acetic acid (8.0 ml.) was stirred for 30 minutes. Sodium cyanoborohydride (1.39 g.) was added and stirring was continued overnight. The reaction mixture was diluted with water (100 ml.). The aqueous layer was extracted with ethyl acetate (3×100 ml.). The combined ethyl acetate solutions were washed successively with 10% v/v aqueous acetic acid, water and brine, dried ($MgSO_4$) and evaporated. The brown oil obtained was purified by chromatography on a column of Kieselgel 60 (70 g.) using 10% v/v methanol in chloroform as eluant. There was thus obtained 4-(1-hydroxy-2-[2-(2-furylcarboxyamido)-1,1-dimethyl-ethylamino]ethyl)catechol dipivaloyl ester (0.70 g.) as a white foam; NMR: 7.70 (1H, broad s, —NHCO); 6.90–7.65 (5H,complex, phenyl-H+furan-3,5-H$_2$); 6.45 (1H, broad s, furan-4H); 4.80 (1H,d, C$\underline{H}$OH); 3.2–3.6 (2H,complex, C$\underline{H}_2$NHCO); 2.70–3.30 (2H,complex, C$\underline{H}_2$NH); 1.25 [24$\overline{H}$, $(CH_3)_3C$— and $(CH_3)_2C$]; microanalysis found: C,57.7; H, 6.6; N,4.8%; $C_{27}H_{38}N_2O_7$ 0.6 $CHCl_3$ requires C, 57.7; H,6.8; N, 4.9%.

The starting material was prepared as follows:

A solution of 2-furoyl chloride (12.0 g.) in dry ether (1.50 ml.) was stirred during the dropwise addition over 30 minutes of a solution of 1,2-diamino-2-methylpropane (9.63 ml.) in dry ether (58 ml.). The reaction mixture was stirred for a further 30 minutes. The solid precipitate was collected by filtration and washed with ether. The residual solid was suspended in hot water (250 ml.) and basified to pH 10 with powdered sodium carbonate. The cooled mixture was extracted with chloroform (3×100 ml.). The combined extracts were dried ($MgSO_4$) and evaporated to give N-(2-amino-2-methyl-propyl)furan-2-carboxamide (10.68 g.) as an oil, which was used without purification.

EXAMPLES 8-10

Using a similar procedure to that described in Example 7, but starting from the appropriate amino compound of formula III, the following esters of formula I ($R^1=R^2$=t-butyl; $R^3=R^4$=methyl, A=direct bond) may be obtained in yields of 15–25%. Where necessary, the ester in free base was dissolved in the minimum volume of ether containing a few drops of ethanol and the solution obtained was just acidified with ethereal hydrogen bromide. Evaporation of the mixture then gave the ester of formula I as the hydrobromide salt:

| Example | Q | Isolated Form | m.p. (°C.) | NMR* |
|---|---|---|---|---|
| 8 | 2-benzo[b]furyl | HBr salt (+ 1.5 $H_2O$) | 172–174 | 7.2–7.90 (5H, complex, benzofuran-H); |
| 9 | 2-benzo[b]thienyl | HBr salt (+ $H_2O$) | foam | 7.10–8.20 (5H, complex, benzothiophene-H) |
| 10 | 3-pyridyl | free base (+ 0.5 $CHCl_3$) | foam | 9.15 (1H,s); 8.85 (2H,d); 8.10 (1H,dd) |

Note*: In addition the following NMR signals were common to the spectrum of each compound: 7.0–7.4 (3H, complex, phenyl-H); 4.8–5.1 (1H, complex, C$\underline{H}$ OH); 2.8–3.9 (4H, complex), 2 × C$\underline{H}_2$NH); 1.20–1.25 [24H, s, $(CH_3)_3C$ + $(CH_3)_2C$].

The starting materials of formula III may be made by a similar procedure to that in Example 1, that is by reacting the appropriate ester of the formula $Q.CO_2R$ (wherein R is methyl or ethyl) with an equimolar quantity of 1,2-diamino-2-methylpropane. They were obtained as oils which were essentially pure by TLC ($SiO_2$: 10–2% v/v methanol in chloroform) and were used without purification.

EXAMPLE 11

Powdered 2-bromo-3′,4′-di(pivaloyloxy)acetophenone (3.37 g.) was added in one portion to a stirred solution of N-(2-amino-2-methylpropyl)pyridine-2-acetamide (3.50 g.) in dry dioxan (35 ml.). The resulting mixture was stirred for 15 minutes and then filtered through diatomaceous earth to remove an oily precipitate. The filtrate [containing 4-(2-[2-methyl-2-(2-pyridylacetamido)propylamino]acetyl)catechol dipivaloylester] was immediately added to ice-cold ethanol (30 ml.) containing sodium borohydride (0.64 g.). The residue from the filtration was washed with ether (15 ml.) and the washings were added to the ethanol/borohydride reaction mixture. This mixture was stirred for 45 minutes at 0° C., then diluted with saturated brine (50 ml.) and extracted with ether (2×100 ml.). The extracts were washed with brine, dried ($MgSO_4$) and evaporated to give a brown oil which was chromatographed on a column of Kieselgel 60 (30 g.), eluting initially with chloroform and then with 10% v/v methanol in chloroform. There was thus obtained 4-(1-hydroxy-2-[1,1-dimethyl-2-(2-pyridylacetamido)-ethylamino]-ethyl)catechol dipivaloyl ester (0.57 g.) as a foam. This was converted to its corresponding hydrogen bromide salt (using ethereal hydrogen bromide and the procedure described in Example 1) which was isolated as a yellow solid (0.28 g.), m.p. 120°–125° C.; NMR: 7.10–8.80 (7H, complex, aromatic+pyridine H), 4.80 (1H, d, C$\underline{\text{H}}$OH), 3.0–4.5 (8H, complex, 2×C$\underline{\text{H}}_2$NH+C$\underline{\text{H}}_2$pyridine+OH+NH), 1.25 [24H, (C$\underline{\text{H}}_3$)$_3$C and (C$\underline{\text{H}}_3$)$_2$C].

The starting amine, N-(2-amino-2-methylpropyl)-pyridine-2-acetamide, was obtained using a similar procedure to that described for the analogous amine in Example 1, but starting from ethyl 2-pyridylacetate and 1,2-diamino-2methylpropane. It was thus obtained as its oily free base, which was essentially pure by TLC (SiO$_2$: 10% v/v methanol in chloroform) and was used without purification.

EXAMPLE 12

A solution of 4-valeryloxy-3-(valeryloxymethyl)-phenylglyoxal (1.67 g.), N-(2-amino-2-methylpropyl)-benzo[b]furan-2-carboxamide (1.1 g.) and glacial acetic acid (29 ml.) in acetonitrile (15 ml.) was stirred for 30 minutes. Sodium cyanoborohydride (0.6 g.) was then added and stirring was continued overnight. The reaction mixture was diluted with water (100 ml.). The aqueous layer was separated and extracted with ethyl acetate (3×100 ml.). The combined ethyl acetate solutions were washed successively with 10% v/v aqeous acetic acid, water and brine, and then dried (MgSO$_4$) and evaporated. The oily residue (2.65 g.) obtained was purified by chromatography on Kieselgel 60 (80 g.) using a gradually increasing concentration of methanol (1–5% v/v) in chloroform as eluant. There was thus obtained 4-(1-hydroxy-2-[2-benzo[b]furylcarboxamido)-1,1-dimethylethylamino]ethyl)-2-(valeryloxymethyl)phenyl valerate, as the oily free base. This material was converted to the corresponding hydrobromide salt (using ethereal hydrogen bromide and the procedure described in Example 1), which was isolated as a foam (0.8 g.); NMR: 8.9–8.2 (4H, broad complex, NHCO, OH+NH$_2$), 7.9–7.0 (8H, complex, aromtic H), 5.05+4.95 (3H, s+d, C$\underline{\text{H}}_2$O.CO+C$\underline{\text{H}}$OH), 3.6–3.0 (complex, CH$_2$N), 2.59 (2H,t,$\overline{\text{CO}}$CH$_2$), 2.30 (2H,t,COCH$_2$), 1.8–1.2 [14H, complex, CH$_2$CH$_2$+(CH$_3$)$_2$C.N.] and 0.92 [6H,t (J=6.6 Hz), C$\underline{\text{H}}_3$CH$_2$].

The starting glyoxal was obtained as follows:

A solution of bromine (2.32 ml.) in chloroform (40 ml.) was added dropwise to a stirred solution of 4-valeryloxy-3-valeryloxymethylacetophenone (15 g.) and t-butyl acetate (6ml.) in chloroform (100 ml.) containing a catalytic amount of anhydrous aluminium chloride. The reaction mixture was stirred for 10 minutes after the addition was complete. Kieselgel 60 (55 g.) was then added and the mixture was evaporated in vacuo. The residual solid was added to the top of a dry column of Kieselgel 60 (1000 g, previously dectivated by addition of 10% w/w water, then equilibrated with 10% v/w of a 5% v/v solution of ethyl acetate in toluene) in a polythene tube. The column was then developed by elution with a solution (1.5 l.) containing 5% v/v ethyl acetate in toluene. The appropriate segment of column (as monitored by thin layer chromatography) was then excised and extracted with ethyl acetate (2×500 ml.). The total extracts were evaporated to give 2-bromo-4'-valeryloxy-3'-valeryloxymethylacetophenone (A) as a syrup (14.8 g.); NMR: 8.1 (1H, d J=2.7 H, aromatic H), 8.02 (1H, dd, aromatic H), 7.28 [1H,d (J=8 O Hz), aromatic H], 5.1 (2H, s, CH$_2$O) 4.4 (2H, s, COCH$_2$Br), 2.2–2.8 (4H, complex CH$_2$CO.O) 1.9–1.0 (8H, complex, CH$_3$C$\underline{\text{H}}_2$CH$_2$) 0.98 (6H, triplet, C$\underline{\text{H}}_3$Ch$_2$CH$_2$).

A solution of A (14.0 g.) in dimethyl sulphoxide was stirred for 3 days. The reaction mixture was diluted with water (200 ml.) and then extracted with ethyl acetate (3×150 ml.). The combined extracts were washed successively with water, saturated sodium bicarbonate solution and brine, and were then dried (MgSO$_4$). Evaporation of the solvent gave 4-valeryloxy-3-(valeryloxymethyl)phenylglyoxal (8.8 g.) which was used directly for condensing with the amine.

EXAMPLE 13

(All parts by weight)

[The following Examples illustrate the preparation of two formulations according to the invention.]

(a) A mixture of finely divided 4-(1-hydroxy-2-[1,1-dimethyl-2-(2-furylcarboxamido)ethylamino]ethyl)-catechol dipivaloyl ester hydrobromide (0.5 parts) in propylene glycol (3.0 parts) and diethylene glycol monoethyl ether (2.0 parts) was added to a stirred mixture of lanolin (4.0 parts) and molten white soft paraffin (90.5 parts). The resulting mixture was allowed to cool to room temperature with rapid stirring until a uniform ointment containing 0.5% by weight of active ingredient for topical administration to humans, was obtained.

(b) A solution of 4-(1-hydroxy-2-[1,1-dimethyl-2-(2-benzo[b]furylcarboxamido)ethylamino]ethyl)catechol dipivaloyl ester hydrobromide (1.0 parts) in ethanol (20 parts) and diethylene glycol monoethyl ether (27 parts) was prepared. Purified water (50 parts) was added to the rapidly stirred solution, followed by carboxypropylmethylene gelling agent ["CARBOPOL" 940 brand, available from B F Goodison Chemical Co., Cleveland, Ohio, USA; 2.0 parts] Stirring was continued until a finely dispersed gel, suitable for topical administration to humans was obtained.

The active ingredient may be replaced by another ester of formula I described herein preferably as its hydrobromide or hydrochloride salt.

In some cases, for example when a salt of a relatively weak acid is used, it may be convenient to form the salt in situ during the formulation process by using the ester of formula I in free base form and adding a molecular equivalent of the appropriate acid to the formulation mixture.

EXAMPLE 14

[Note: this Example demonstrates the topical anti-inflammatory properties of representative esters of formula I and in particular the effect of repeated topical applications on their anti-inflammatory properties in the croton oil induced inflammation test in the mouse.]

(a) The topical anti-inflammatory activity of a test compound was demonstrated as follows:

A 4% v/v solution of croton oil in (acetone) was prepared. A portion (10 μl.) of this solution was applied to the right ear of an albino mouse (Alderley Park Strain, specific pathogen free). This was followed by immediate application of a portion (10 μl.) of a solution of test compound in ethanol to the same ear of the mouse. This procedure was repeated for a total of ten mice.

After 4 hours the mice were sacrificed and both ears from each mouse were removed and weighed. The increase in weight of the right over the left ear for each mouse was then determined and an average obtained for the group as a whole. This was then compared with the increase in weightof the right over the left ear in a control group of 10 mice which had received croton oil and ethanol, but no test compound. The percentage inhibition of croton oil induced inflammation was then calculated for the test compound.

This procedure was then repeated using different concentrations of test compound in ethanol to determine the amount of test compound per ear which inhibited the inflammation by 50% ($IC_{50}$).

(b) An indication of the effect of repeated topical application of a test compound on its anti-inflammatory properties was obtained as follows:

Procedure (a) above was repeated, except that each animal in the test group received a total of four applications of test compound at a concentration four times greater than the $IC_{50}$ of that test compound as follows:

first application received 3 days before croton oil;
second application received 2 days before croton oil;
third application received 1 day before croton oil; and
fourth application received immediately after croton oil.

The percentage reduction in inflammation relative to a control group was then compared to that in a group of animals which had received only a single application of test compound immediately after croton oil.

The following results were obtained for:
(i) three novel, representative esters of formula I included in the invention;
(ii) three novel esters of formula I structurally similar to those in (i) but outside the scope of the invention; and
(iii) a known catechol diester of formula I described in UK patent specification Ser. No. 1591618.

| Category | Q* | (a) $IC_{50}$ (μg/ear) | Application rate (μg/ear) | (b) Single Appln (%)** | Four Applns (%)** |
|---|---|---|---|---|---|
| i | 2-furyl | 13 | 50 | 60 | 64 |
| i | 2-benzo[b]furyl | 11 | 50 | 61 | 59 |
| i | 2-benzo[b]thenyl | 23 | 90 | 64 | 65 |
| ii | 3-furyl | 2 | 10 | 65 | 45 |
| ii | 4-chloro-2-pyridyl | 7 | 30 | 68 | 33 |
| ii | 2-thienyl | 7 | 30 | 71 | 33 |
| iii | phenoxymethyl | 2.5 | 10 | 60 | 23 |

* $R^1$-$R^2$ = t-butyl; $R^3$ = $R^4$ = methyl; A = direct bond
** Percentage reduction in croton oil induced inflammation after 1 or 4 applications of test compound.

The above results demonstrate a significant fall in anti-inflammatory effect for both the (ii) and (iii) compounds after four topical applications at a concentration approximately four times greater than the $IC_{50}$. By contrast no significant reduction in anti-inflammatory effect occurred with the esters (i) included in the present invention.

What is claimed is:
1. A diester of the formula:

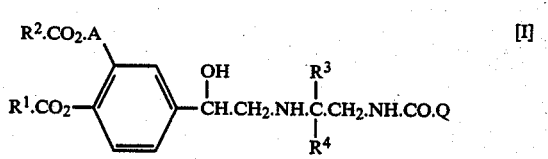

wherein $R^1$ and $R^2$ are independently (3-5C)alkyl; and
(i) A is a direct bond, $R^3$ and $R^4$ are hydrogen, and Q is 2-thienyl, 2-benzo[b]thienyl or 2-thienylmethyl;
(ii) A is a direct bond, $R^3$ and $R^4$ are methyl and Q is 2-furyl, 2-benzo[b]furyl or 2-benzo[b]thienyl; or
(iii) A is methylene, $R^3$ and $R^4$ are methyl and Q is 2-benzo[b]furyl or 2-benzo[b]thienyl; or a pharmaceutically acceptable acid-addition salt thereof.

2. A diester as claimed in claim 1 wherein $R^1$ and $R^2$ are independently isopropyl, n-propyl, isobutyl, t-butyl, n-butyl or 2,2-dimethylpropyl.

3. A diester as claimed in claim 1 wherein $R^1$ and $R^2$ have the same values.

4. A diester as claimed in claim 1 wherein $R^1$ and $R^2$ are both t-butyl and A is a direct bond.

5. A diester as claimed in claim 1 wherein A is a direct bond, $R^3$ and $R^4$ are both methyl and Q is 2-furyl, 2-benzo[b]furyl or 2-benzo[b]thienyl.

6. A diester of formula I set out in claim 1 selected from 4-(1-hydroxy-2-[1,1-dimethyl-2-(2-furylcarboxamido)ethylamino]ethyl)catechol dipivaloyl ester, 4-(1-hydroxy-2-[1,1-dimethyl-2-(2-benzo[b]furylcarboxamido)ethylamino]ethyl)catechol dipivaloyl ester, 4-(1-hydroxy -2-[1,1-dimethyl-2-(2-benzo[b]thienylcarboxamido)ethylamino]ethyl)catechol dipivaloyl ester; and the pharmaceutically acceptable acid-addition salts thereof.

7. A pharmaceutically acceptable acid-addition salt as claimed in claim 1 which is selected from addition salts with hydrochloric, hydrobromic, phosphoric, sulphuric, oxalic, adipic, tartaric, fumaric, citric, acetic, salicylic, benzoic, naphthoic and methanesulphonic acids.

8. A pharmaceutical composition which comprises an effective amount of a diester of formula I, or a pharmaceutically acceptable acid-addition salt thereof, as claimed in claim 1 in association with a pharmaceutically acceptable excipient and in a form suitable for topical administration.

9. A composition as claimed in claim 8 wherein the active ingredient is a diester of formula I, or a pharmaceutically acceptable acid-addition salt thereof, as claimed in claim 6.

10. A method for the production of an anti-inflammatory effect in an area of skin of a warm-bloodedanimal requiring such treatment which comprises topical administration to said area of an effective amount of an ester of formula I or a pharmaceutically acceptable acid-addition salt thereof as claimed in claim 1.

* * * * *